(12) United States Patent
Mou et al.

(10) Patent No.: US 11,077,265 B2
(45) Date of Patent: Aug. 3, 2021

(54) POSITIVE AIRWAY PRESSURE APPARATUS

(71) Applicant: Microjet Technology Co., Ltd., Hsinchu (TW)

(72) Inventors: Hao-Jan Mou, Hsinchu (TW);
Hsuan-Kai Chen, Hsinchu (TW);
Wei-Ming Lee, Hsinchu (TW);
Chi-Feng Huang, Hsinchu (TW);
Yung-Lung Han, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 316 days.

(21) Appl. No.: 16/243,741

(22) Filed: Jan. 9, 2019

(65) Prior Publication Data

US 2019/0282772 A1  Sep. 19, 2019

(30) Foreign Application Priority Data

Mar. 16, 2018 (TW) .................................. 107109152

(51) Int. Cl.
*A61M 16/00* (2006.01)
*A61M 16/06* (2006.01)

(52) U.S. Cl.
CPC .... *A61M 16/0057* (2013.01); *A61M 16/0003* (2014.02); *A61M 16/024* (2017.08);
(Continued)

(58) Field of Classification Search
CPC .......... A61M 16/0051; A61M 16/0057; A61M 16/0066; A61M 16/0069; A61M 16/022;
(Continued)

(56) References Cited

U.S. PATENT DOCUMENTS

| 10,137,264 B2 | 11/2018 | Darby et al. |
| 2006/0051218 A1* | 3/2006 | Harttig .............. A61M 5/14228 417/412 |

(Continued)

FOREIGN PATENT DOCUMENTS

| CN | 201275352 Y | 7/2009 |
| CN | 106620978 A | 5/2017 |

(Continued)

OTHER PUBLICATIONS

Extended European Search Report, dated Jun. 19, 2019, for European Application No. 19151004.9.

*Primary Examiner* — Annette Dixon
(74) *Attorney, Agent, or Firm* — Birch, Stewart, Kolasch & Birch LLP (57) ABSTRACT

A positive airway pressure apparatus is disclosed and includes a mask, a micro pump and a processor. The mask is fastened on a user's face and is spatially corresponding to an airway opening of the user, so as to form a closed space. The micro pump is assembled with the cover and is in fluid communication with the exterior of the mask. The processor transmits an actuation control signal to the micro pump so as to actuate the micro pump. Consequently, air is transported into the closed space from the exterior of the mask, and a positive pressure airflow is formed and flows into the airway of the user. A pressure sensor is disposed within the closed space to detect the pressure of the closed space, so that the processor can determine the respiratory state of the user and control the air pressure output of the micro pump correspondingly.

9 Claims, 9 Drawing Sheets

(52) U.S. Cl.
CPC ..... *A61M 16/06* (2013.01); *A61M 2016/0027* (2013.01); *A61M 2016/0039* (2013.01); *A61M 2205/0294* (2013.01); *A61M 2205/50* (2013.01); *A61M 2205/8206* (2013.01); *A61M 2205/8237* (2013.01); *A61M 2205/8262* (2013.01); *A61M 2209/088* (2013.01); *A61M 2230/42* (2013.01)

(58) Field of Classification Search
CPC ............ A61M 16/024; A61M 16/0493; A61M 16/06; A61M 16/0666; A61M 16/0683; A61M 16/107; A61M 16/108; A61M 16/1085; A61M 16/16; A61M 16/161; A61M 16/20; A61M 16/208; A61M 2016/0021; A61M 2016/0027; A61M 2016/003; A61M 2205/0244; A61M 2205/0266; A61M 2205/12; A61M 2205/3375; A61M 2205/3569; A61M 2205/3592; A61M 2205/3673; A61M 2205/42; A61M 2205/50; A61M 2205/581; A61M 2205/587; A61M 2205/8206; A61M 2205/8237; A61M 2209/088; A61M 2230/50; A61M 5/14228; A61B 18/006; B01L 2300/0816; B01L 2400/0481; B01L 3/50273; F04B 19/006; F04B 43/043; F04B 43/046; F04B 45/043; F04B 45/047; F04F 7/00; F16K 1/18; G01N 2035/1034
See application file for complete search history.

(56) References Cited

U.S. PATENT DOCUMENTS

| | | | |
|---|---|---|---|
| 2006/0096596 A1* | 5/2006 | Occhialini | A61M 16/16 128/204.18 |
| 2008/0216835 A1* | 9/2008 | McGinnis | A61M 16/107 128/204.23 |
| 2011/0076170 A1* | 3/2011 | Fujisaki | F04B 43/046 417/415 |
| 2015/0217073 A1 | 8/2015 | Nitta et al. | |
| 2015/0267695 A1* | 9/2015 | Marsh | F16K 1/18 128/205.24 |
| 2017/0222121 A1 | 8/2017 | Chen et al. | |

FOREIGN PATENT DOCUMENTS

| | | |
|---|---|---|
| CN | 106924849 A | 7/2017 |
| EP | 1655052 A2 | 5/2006 |
| TW | M553219 U | 12/2017 |

* cited by examiner

POSITIVE AIRWAY PRESSURE APPARATUS

FIELD OF THE INVENTION

The present disclosure relates to a positive airway pressure apparatus, and more particularly to a positive airway pressure apparatus having a micro pump for producing a positive pressure airflow.

BACKGROUND OF THE INVENTION

Nowadays, for patients with moderate to severe obstruct sleep apnea (OSA), the mainstream therapy in the medical field is to supply a positive airway airflow by a positive airway pressure apparatus (also known as Continuous Positive Airway Pressure apparatus, CAPA apparatus), so as to expand the patient's respiratory tract to achieve the effect of driving the breath. This treatment can effectively improve respiratory abnormalities including Apnea and Hypopnea, effectively improve the sleep quality of patients, and further reduce the probability of a cardiovascular disease (CVD) and a brain attack.

Figure 1:
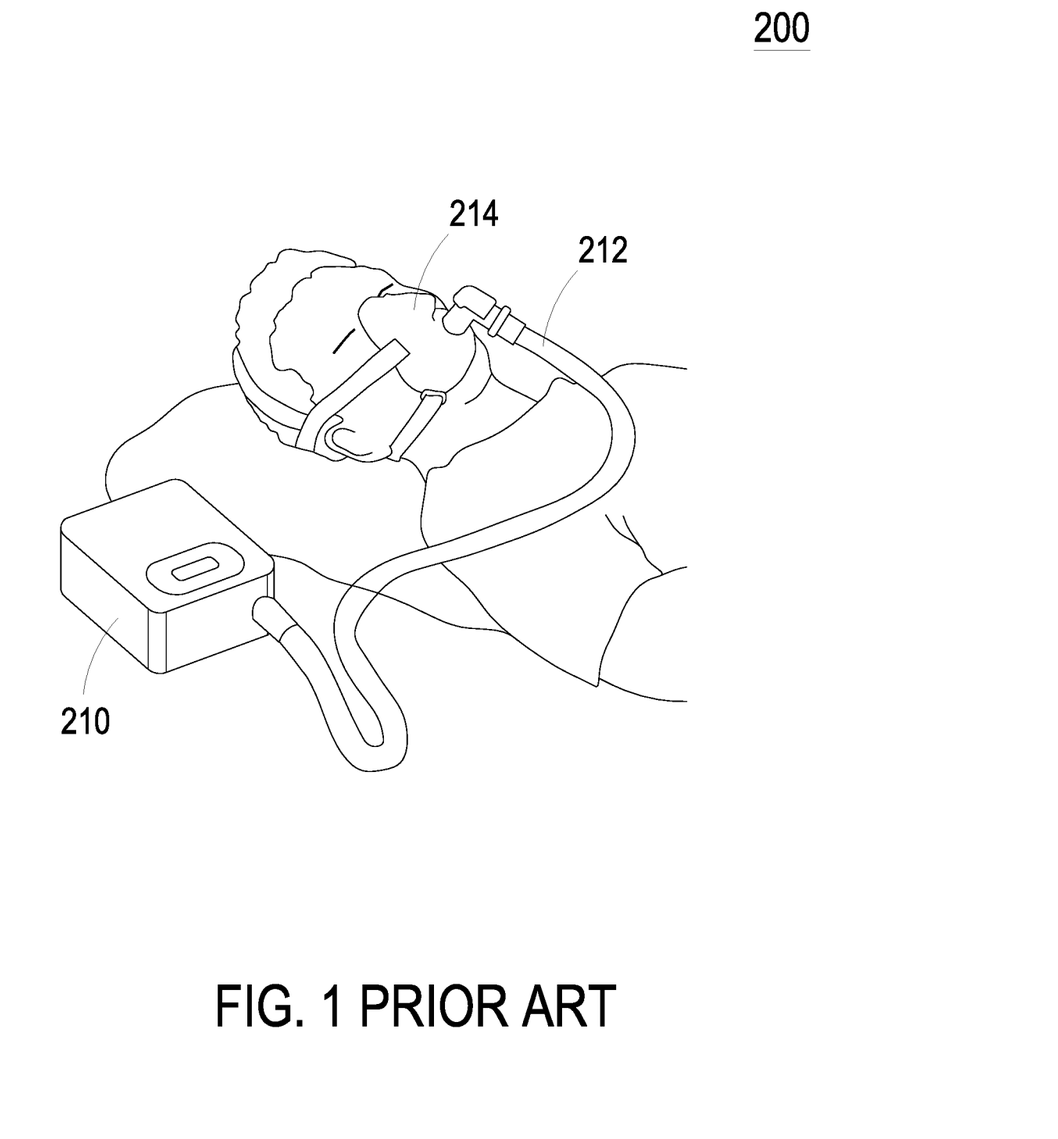
FIG. 1 is a schematic diagram showing a positive airway pressure apparatus in use according to the prior art.

Please refer to FIG. 1, which is a schematic diagram showing a positive airway pressure apparatus in use according to the prior art. The conventional positive airway pressure apparatus 200 includes a body 210 having a vacuum pump disposed therein. The body 210 has the size approximately similar to that of a general notebook and is connected with a breathing mask 214 through a ventilation hose 212. Patients with apnea must wear the breathing mask 214 throughout their sleep and keep the body 210 in an activated state. The vacuum pump in the body 210 continuously injects air with a positive pressure ranged between 4 cmH$_2$O to 20 cmH$_2$O to the patient's respiratory tract through the ventilation hose 212.

However, the positive airway pressure apparatus 200 of the prior art has the disadvantages of wearing discomfort and inconvenience in carrying out due to construction and volume factors. Since the positive airway pressure apparatus 200 needs to introduce the air into the breathing mask 214 through the ventilation hose 212, the user needs to keep a fixed sleeping posture to prevent the ventilation hose 212 from being pressed, causing the air to be unsatisfactory or stopping the supply of the air due to the user's action during sleep. The patient's poor sleep posture is caused to press the ventilation hose 212 and the patient fails to get in deep sleep. Most of the patients receiving positive pressure breathing therapy fail to wear the positive airway pressure apparatus 200 for a long period of time during every sleeping night. The wearer's average wearing time per night is also much smaller than the doctor's recommended wearing time. The main cause of the patient's inability to wear for a long period of time or wear all night is the wearing discomfort caused by the positive airway pressure apparatus 200. The patient wearing the positive airway pressure apparatus 200 not only fails to turn over during sleep, but also has to endure the feeling of connecting a foreign matter to the body. In addition, the patient must carry the entire positive airway pressure apparatus 200 when going out to play, and must choose a place having a power supply to stay overnight. It is very inconvenient for those who need to go out to stay overnight or long-haul flights.

In view of the above-mentioned issues of the conventional positive airway pressure apparatus 200, the patient often interrupts the treatment and the treatment effect is influenced. Therefore, it is urgent and necessary to improve the comfort and portability of the positive airway pressure apparatus 200.

SUMMARY OF THE INVENTION

An object of the present invention is to provide an improved positive airway pressure apparatus. A micro pump is directly coupled with a mask to replace the conventional positive airway pressure apparatus, which includes the breathing mask and the vacuum pumps connected with each other through the ventilation hose. The micro pump supplies an air pressure with sufficient output value to replace the traditional vacuum pump, and allows the air outside the mask to be pumped into the mask to form a positive pressure airflow, thereby eliminating the use of the ventilation hose and reducing the volume of the overall apparatus. In this way, the discomfort of wearing a positive airway pressure apparatus during sleep can be reduced, and the portability of the positive airway pressure apparatus can be improved.

In accordance with an aspect of the present disclosure, there is provided a positive airway pressure apparatus including a mask, a micro pump and a processor. The mask has a space and is worn by a user to cover an airway opening (i.e., the mouth and the nose of the user) on the user's face so that a closed space is defined by the space of the mask and the user's face. The micro pump is coupled to the mask and in fluid communication with the exterior of the mask. The processor is electrically connected to the micro pump. When the processor transmits an actuation control signal to the micro pump, the micro pump is actuated in response to the actuation control signal and transports air from the exterior of the mask into the closed space to form the positive pressure airflow to the user.

In an embodiment, the micro pump is a piezoelectric actuating pump. The piezoelectric actuating pump includes an air inlet plate, a resonance plate and a piezoelectric actuator. In response to an applied voltage, the piezoelectric actuator and a movable part of the resonance plate are driven to vibrate in resonance. The air from at least one inlet of the air inlet plate is converged to a convergence chamber along the at least one convergence channel and flows into the chamber space through a central aperture of the resonance plate, so as to form a positive pressure airflow transported downwardly. The piezoelectric actuator includes a suspension plate, an outer frame arranged around the suspension plate, at least one bracket connected between the suspension plate and the outer frame, and a piezoelectric element. The piezoelectric element is attached on a surface of the suspension plate to drive the suspension plate to undergo the bending vibration in response to an applied voltage.

In an embodiment, the positive airway pressure apparatus further includes a pressure sensor disposed within the space of the mask to measure a pressure of the closed space to generate a detected pressure value and transmit the detected pressure value to the processor. The detected pressure value is compared with a preset pressure value by the processor, so as to generate a pressure control signal according to the comparison result and transmit the pressure control signal to the micro pump, thereby regulating an air pressure output of the micro pump and ensuring the pressure of the closed space complying with the preset pressure value. Furthermore, a plurality of detected pressure values are generated and transmitted to the processor by the pressure sensor continuously. The detected pressure values are used to analyze a respiratory state of the user by the processor, so as to generate a pressure control signal according to the respiratory state and transmit the pressure control signal to the micro pump, thereby increasing or decreasing an air pressure output of the micro pump. When the processor determines that the respiratory state is an alternate point of inhalation and exhalation, the pressure control signal is generated and transmitted to the micro pump to decrease the air pressure output of the micro pump. When the processor determines that the respiratory state is an abnormal state, the pressure control signal is generated and transmitted to the micro pump to increase the air pressure output of the micro pump.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 2:
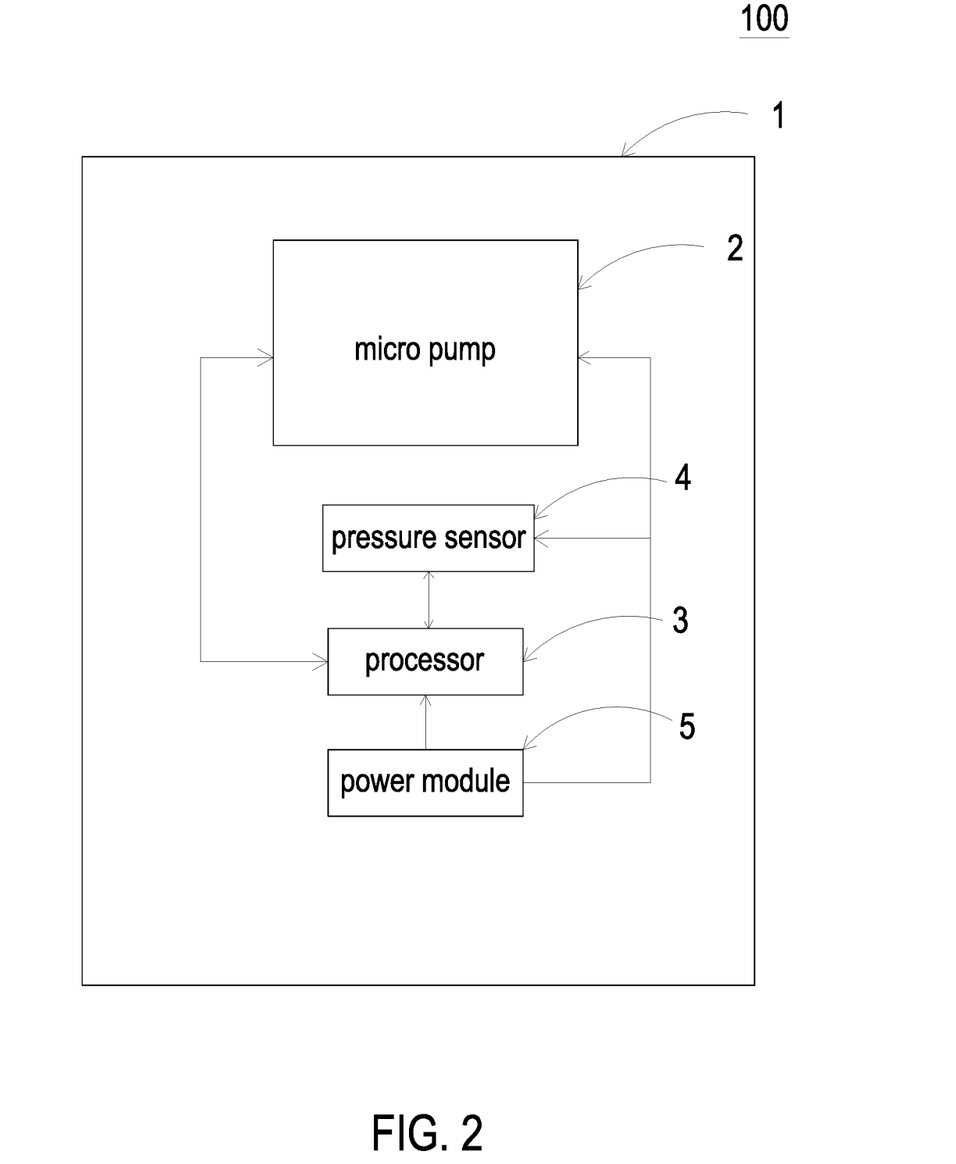
FIG. 2 is a block diagram of a positive airway pressure apparatus according to an embodiment of the present disclosure.

Please refer to FIG. 2. The present discourse provides a positive airway pressure apparatus 100 for producing at least one positive pressure airflow. The number of the positive pressure airflow is exemplified by one in the following embodiments but not limited thereto. The positive pressure airflow can also be provided in a plurality of numbers. The positive airway pressure apparatus 100 includes at least one mask 1, at least one micro pump 2, at least one processor 3, at least one space and at least one actuation control signal. The numbers of the mask 1, the micro pump 2, the processor 3, the space and the actuation control signal are exemplified by one for each in the following embodiments but not limited thereto. It should be noted that each of the mask 1, the micro pump 2, the processor 3, the positive pressure airflow, the space and the actuation control signal can also be provided in plural numbers.

Figure 3:
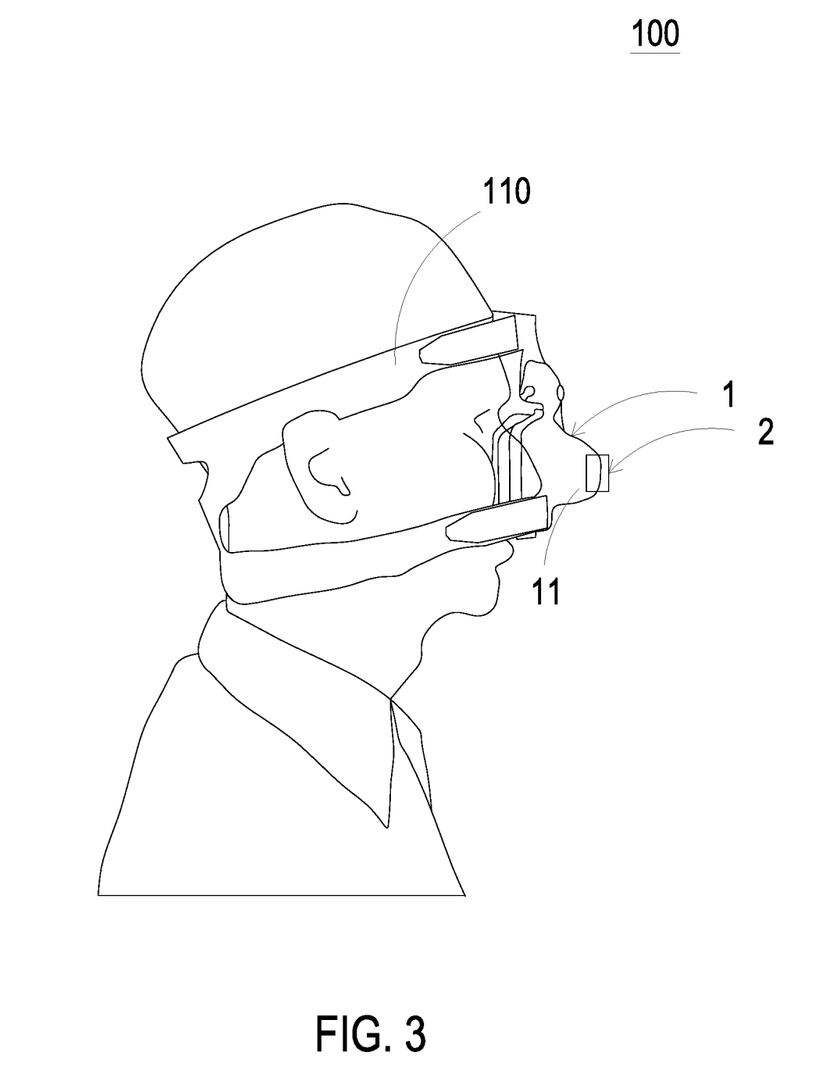
FIG. 3 is a schematic diagram showing the positive airway pressure apparatus in use according to the embodiment of the present disclosure.

Please refer to FIGS. 2 and 3. FIG. 2 is a block diagram of a positive airway pressure apparatus according to an embodiment of the present disclosure. FIG. 3 is a schematic diagram showing the positive airway pressure apparatus in use according to the embodiment of the present disclosure. As shown in the drawings, the positive airway pressure apparatus 100 includes a mask 1, a micro pump 2, a processor 3, a pressure sensor 4 and a power module 5. The mask 1 has a space and the mask 1 includes a head fastening device 110. The mask 1 is fastened on a user's face through the head fastening device 110 and the space of the mask 1 is spatially corresponding to the user's airway opening to form a closed space 11. The micro pump is embedded in and assembled with the mask 1, so as to transport air from the exterior of the mask 1 into the closed space 11. Preferably but not exclusively, the micro pump 2 is a piezoelectric actuating pump. The structure and the actions of the micro pump 2 will be described in detail later. The processor 3 is electrically connected to the micro pump 2 and the pressure sensor 4. Preferably but not exclusively, the processor 3 and the micro pump 2 are assembled together as a one-piece module embedded within the mask 1. Alternatively, the processor 3 and the micro pump 2 are disposed separately and electrically connected with each other through a wire.

In the embodiment, the pressure sensor 4 is disposed within the space of the mask 1 and electrically connected to the processor 3. Preferably but not exclusively, the pressure sensor 4 and the micro pump 2 are assembled together as a one-piece module embedded within the mask 1. Alternatively, the pressure sensor 4 and the micro pump 2 are separately disposed within the mask 1. The pressure sensor 4 is used for measuring a pressure of the closed space 11 to generate a detected pressure value and transmit the detected pressure value to the processor 3.

In the embodiment, the power module 5 is used for storing electrical energy and outputting electrical energy. The electrical energy is provided to the processor 3, so that the processor 3 can control the actuation of the micro pump 2. In an embodiment, the power module 5 is further connected to an external power supply device (not shown), and the external power supply device transmits the electrical energy to the power module 5 for storing. The external power supply device can transmit the electrical energy to the power module 5 by means of a wired transmission technology or transmit the electrical energy to the power module 5 by a wireless transmission technology, but not limited thereto.

In the embodiment, when the positive airway pressure apparatus 100 is operated to start, the processor 3 transmits an actuation control signal to the micro pump 2. The micro pump 2 is actuated in response to the actuation control signal and transports air from the exterior of the mask 1 into the closed space 11 to form a positive pressure airflow.

In the embodiment, when the processor 3 receives the detected pressure value from the pressure sensor 4, the detected pressure value is compared with a preset pressure value by the processor 3. Preferably but not exclusively, the preset pressure value is preset by the user and ranged from 4 $cmH_2O$ to 20 $cmH_2O$. If there is a deviation between the detected pressure value and the preset pressure value in the comparison result, the processor 3 generates a pressure control signal according to the deviation and transmits the pressure control signal to the micro pump 2, thereby slightly regulating the air pressure output of the micro pump 2. It is ensured that the pressure in the closed space 11 complies with the preset pressure value, thereby eliminating the deviation.

In another embodiment, the processor 3 continuously receives a plurality of detected pressure values from the pressure sensor 4 and transfers the plurality of detected pressure values to an airflow waveform. The processor 3 analyzes a respiratory state of the user according to the airflow waveform, and predicts whether any respiratory abnormality tends to occur. The respiratory abnormality can be for example but not limited to obstructive breathing, shallow breathing or snoring. When the processor 3 determines that the respiratory state is an alternate point of inhalation and exhalation, the pressure control signal is preset to generate and transmitted to the micro pump 2 to decrease the air pressure output of the micro pump 2. Preferably but not exclusively, the decreasing pressure value is preset and ranged from 1 cmH2O to 30 cmH2O. Alternatively, when the processor 3 determines that the respiratory state is an abnormal state, namely it predicts a respiratory abnormality of the user tends to occur, the pressure control signal is preset to generate and transmitted to the micro pump 2 to increase the air pressure output of the micro pump 2. Preferably but not exclusively, the increasing pressure value is 1 cmH2O.

Please refer to FIGS. 4A to 5A. Preferably but not exclusively, the micro pump 2 described above is a piezoelectric actuating pump. The maximum air pressure output of the micro pump 2 can reach 350 mmHg (about 476 $cmH_2O$), which can meet the pressure output requirement of positive airway pressure therapy between 4 $cmH_2O$ and 20 $cmH_2O$. The piezoelectric actuating pump described above includes an air inlet plate 21, a resonance plate 22, a piezoelectric actuator 23, an insulation plate 24 and a conducting plate 25 stacked and assembled sequentially. The air inlet plate 21 has at least one inlet 21a, at least one convergence channel 21b and a convergence chamber 21c. The numbers of the inlet 21a and the convergence channel 21b are the same. In the embodiment, the numbers of the inlets 21a and the convergence channels 21b are exemplified by four for each, but not limited thereto. The four inlets 21a run through the corresponding convergence channels 21b and the four convergence channels 21b converge to the convergence chamber 21c.

Figure 4A:
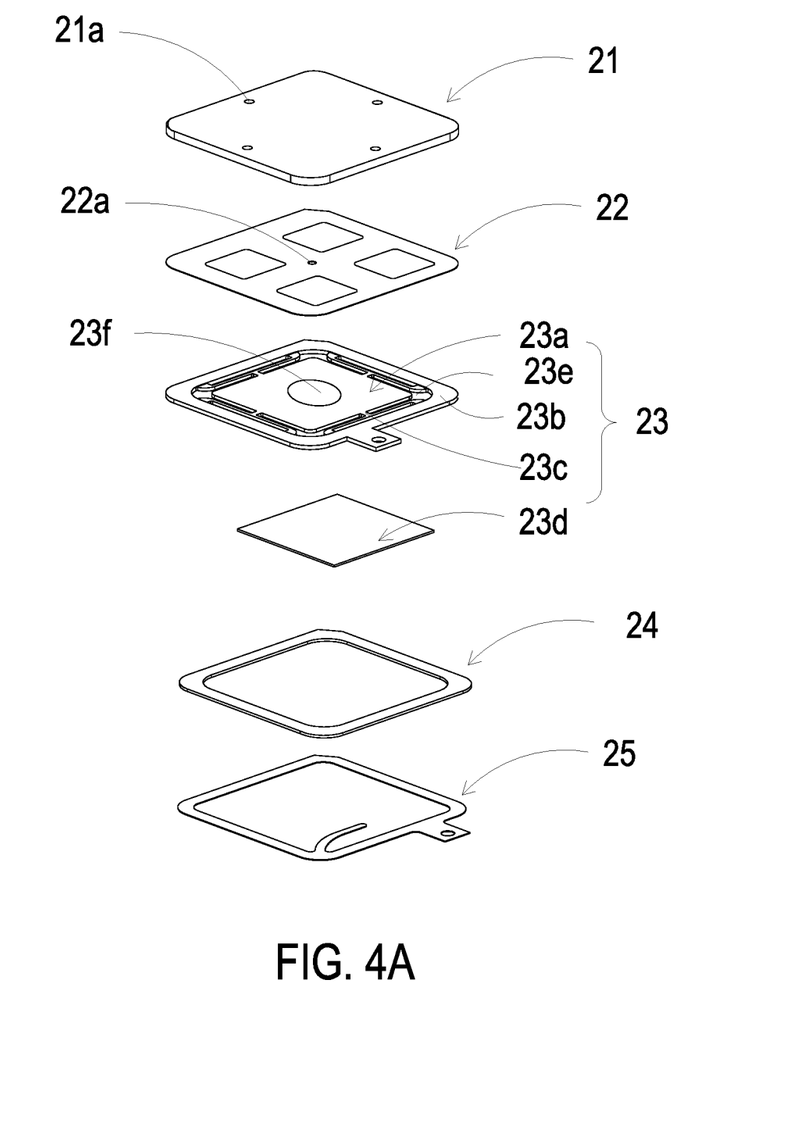
FIG. 4A is an explored view showing a micro pump in a semi-finished state according to the embodiment of the present disclosure.
Figure 4B:
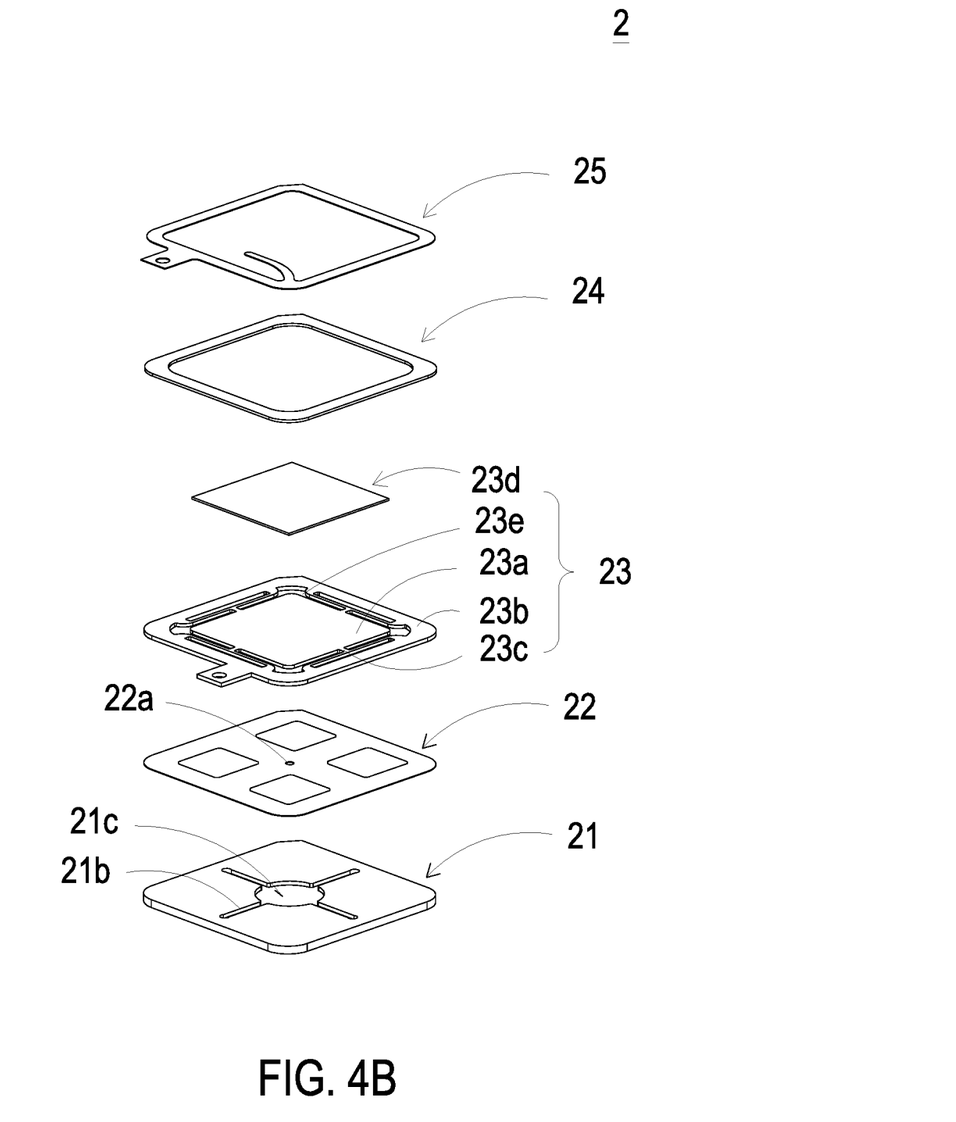
FIG. 4B is another explored view showing the micro pump in a semi-finished state according to the embodiment of the present disclosure and taken at a different observation angle.
Figure 5A:
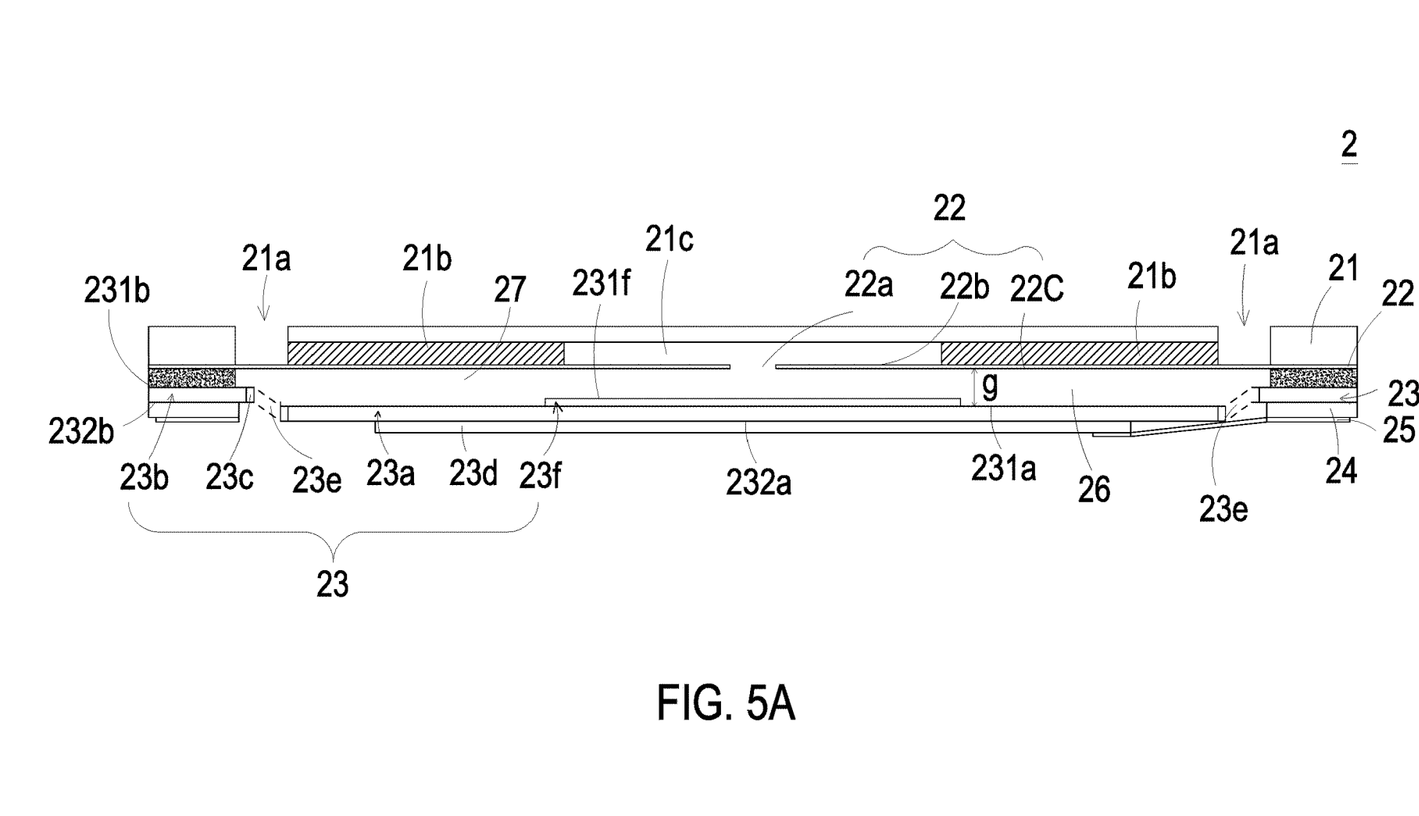
FIG. 5A is a schematic cross-sectional view illustrating the micro pump according to the embodiment of the present disclosure.

In the embodiment, the resonance plate 22 is coupled to the air inlet plate 21 by means of for example attaching. Moreover, the resonance plate 22 includes a central aperture 22a, a movable part 22b and a fixed part 22c. The central aperture 22a is located at the center of the resonance plate 22 and facing the convergence chamber 21c of the air inlet plate 21. The movable part 22b surrounds the central aperture 22a and is also facing the convergence chamber 21c. The fixed part 22c is a peripheral portion of the resonance plate 22 which is attached and fixed on the air inlet plate 21.

In the embodiment, the piezoelectric actuator 23 includes a suspension plate 23a, an outer frame 23b, at least one bracket 23c, a piezoelectric element 23d, at least one vacant space 23e and a bulge 23f. The suspension plate 23a has a first surface 231a and a second surface 232a. The first surface 231a is opposite to the second surface 232a. The outer frame 23b is arranged around the suspension plate 23a. The outer frame 23b has a coupling surface 231b and a bottom surface 232b. The at least one bracket 23c is connected between the suspension plate 23a and the outer frame 23b for elastically supporting the suspension plate 23a. The vacant spaces 23e are formed among the suspension plate 23a, the outer frame 23b and the brackets 23c for the air flowing therethough.

In addition, the suspension plate 23a has the bulge 23f disposed on the first surface 231a. In the embodiment, the bulge 23f is formed by etching the peripheral edge of the bulge 23f and the connection parts adjacent to the brackets 23c to make it concave, so that the bulge 23f of the suspension plate 23a is higher than the first surface 231a and a stepped structure is formed.

Please refer to FIG. 5A again. In the embodiment, the suspension plate 23a is formed by stamping to make it concave downwardly and away from the resonance plate 22. The concave distance can be adjusted through the at least one bracket 23c formed between the suspension plate 23a and the outer frame 23b. Consequently, the top surface 231f of the bulge 23f disposed on the suspension plate 23a and the coupling surface 231b of the outer frame 23b are non-coplanar. Namely, the top surface 231f of the bulge 23f is lower than the coupling surface 231b of the outer frame 23b, and the second surface 232a of the suspension plate 23a is lower than the bottom surface 232b of the outer frame 23b. In the embodiment, the piezoelectric element 23d is attached on the second surface 232a of the suspension plate 23a and aligned with the bulge 23f. In response to an applied voltage, the piezoelectric element 23d is deformed by the piezoelectric effect, and drives the suspension plate 23a to undergo the bending vibration.

By utilizing a small amount of adhesive applied to the coupling surface 231b of the outer frame 23b, the piezoelectric actuator 23 is attached to the fixed part 22c of the resonance plate 22 by heat pressing, thereby assembling the piezoelectric actuator 23 and the resonance plates 22 in combination.

In addition, the insulation plate 24 and the conducting plate 25 are both thin frame-shaped sheets, which are sequentially stacked under the piezoelectric actuator 23. In the embodiment, the insulation plate 24 is attached to the bottom surface 232b of the outer frame 23b of the piezoelectric actuator 23.

Please refer to FIG. 5A again. After the air inlet plate 21, the resonance plate 22, the piezoelectric actuator 23, the insulation plate 24 and the conducting plate 25 are stacked and assembled sequentially, a chamber gap g is formed between the first surface 231a of the suspension plate 23a and the resonance plate 22. Since the chamber gap g will influence the transportation effect of the micro pump 2, it is very important to maintain a fixed chamber gap g for providing stable transportation efficiency. As a result of the stamping process, the suspension plate 23a of the micro pump 2 is made concave downwardly. Consequently, the first surface 231a of the suspension plate 23a and the coupling surface 231b of the outer frame 23b are non-coplanar. Namely, the first surface 231a of the suspension plate 23a is lower than the coupling surface 231b of the outer frame 23b, and the second surface 232a of the suspension plate 23a is lower than the bottom surface 232b of the outer frame 23b. Thus, the suspension plate 23a of the piezoelectric actuator 23 has improved structure as being recessed in a direction away from the resonance plate 22 to form a chamber space 26, which constructs the adjustable chamber gap g between the suspension plate 23a and the resonance plate 22. In this way, the required chamber gap g can be achieved by adjusting the concave distance of the suspension plate 23a of the piezoelectric actuator 23. It benefits to simplify the structural design of mechanism of adjusting the chamber gap g, and also achieves the advantages of simplifying the process and shortening the processing time.

Figure 5B:
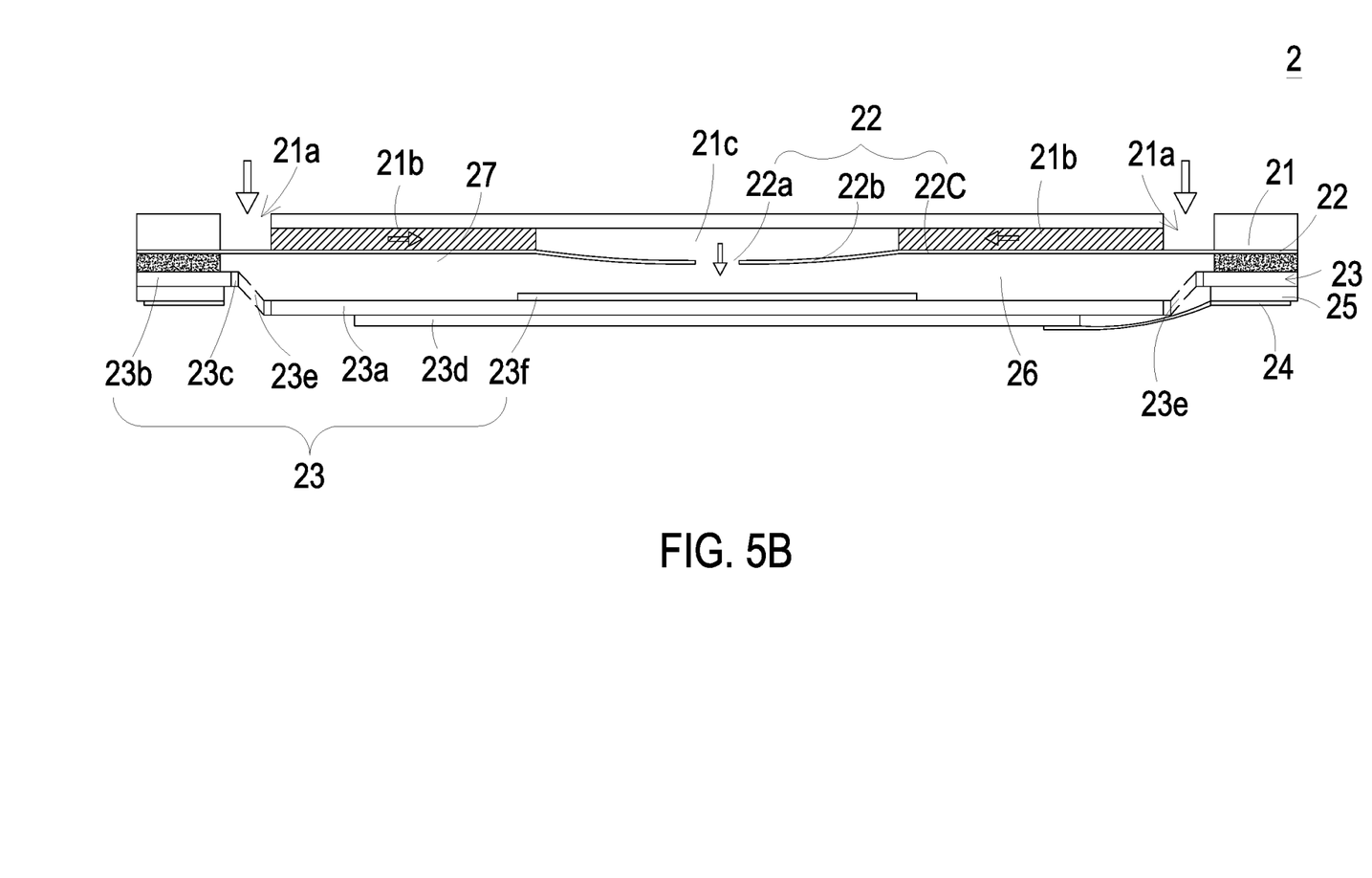
FIGS. 5B to 5D are schematic cross-sectional views illustrating the actions of micro pump according to the embodiment of the present disclosure.
Figure 5C:
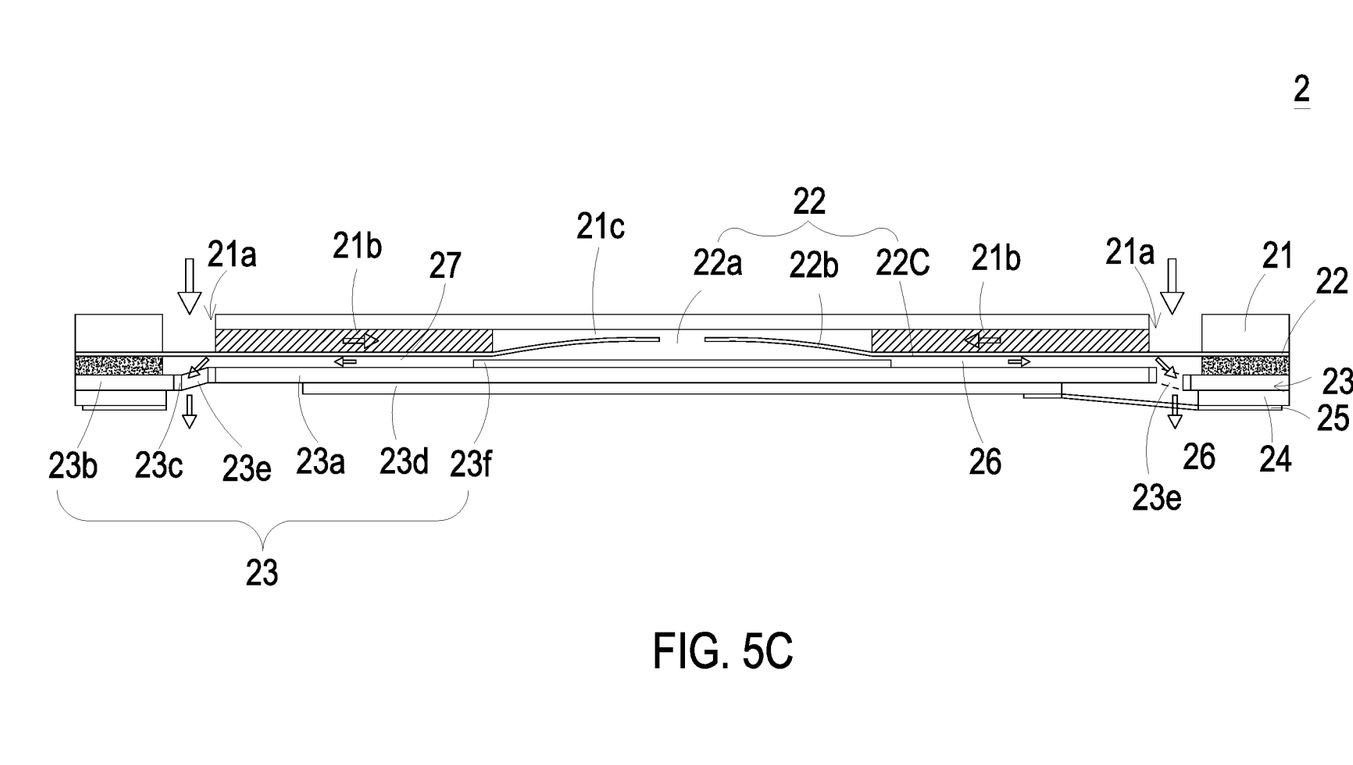
Figure 5D:
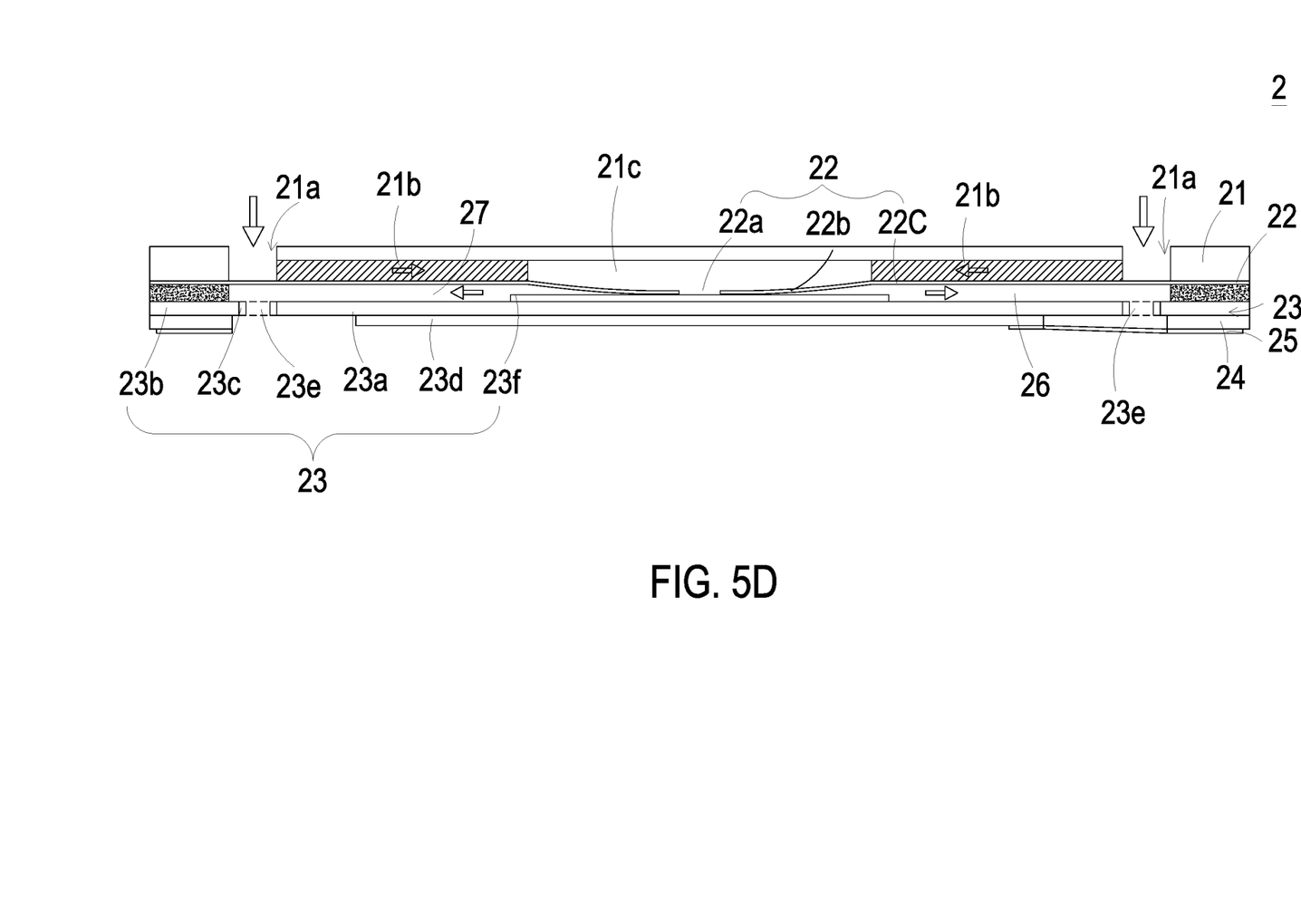

FIGS. 5B and 5D are schematic cross-sectional views illustrating the actions of micro pump according to the embodiment of the present disclosure. Please refer to FIG. 5. When the piezoelectric element 23d of the piezoelectric actuator 23 is deformed in response to an applied voltage, the suspension plate 23a is driven to displace in the direction away from the air inlet plate 21. In that, the volume of the chamber space 26 is increased, a negative pressure is formed in the chamber space 26, and the air in the convergence chamber 21*c* is inhaled into the chamber space 26. At the same time, the resonance plate 22 is in resonance and thus displaced synchronously in the direction away from the air inlet plate 21. Thereby, the volume of the convergence chamber 21*c* is increased. Since the air in the convergence chamber 21*c* flows into the chamber space 26, the convergence chamber 21*c* is also in a negative pressure state, and the air is sucked into the convergence chamber 21*c* by flowing through the inlet 21*a* and the convergence channel 21*b*. Please refer to FIG. 5C. The piezoelectric element 23*d* drives the suspension plate 23*a* to be displaced toward the air inlet plate 21 to compress the chamber space 26. Thus, the air contained in the chamber space 26 is transported to flow through the vacant spaces 23*e* in the direction away from the air inlet plate 21 and it achieves the effect of air transportation. Similarly, the resonance plate 22 is actuated in resonance by the suspension plate 23*a* and displaced toward the air inlet plate 21. Thus, the air contained in convergence chamber 21*c* is compressed synchronously to the chamber space 26. Finally, as shown in FIG. 5D, when the suspension plate 23*a* is driven to displace in the direction away from the air inlet plate 21 and the resonance plate 22 is also driven to displace in the direction away from the air inlet plate 21 at the same time. In that, the resonance plate 22 pushes the air in the chamber space 26 toward the vacant space 23*e*, and the volume of the convergence chamber 21*c* is increased. Thus, the air can continuously flow through the inlet 21*a* and the convergence channel 21*b* and be converged in the convergence chamber 21*c*. By repeating the actions of the micro pump 2 shown in the above continuously, the micro pump 2 can continuously inhale the air through the inlet 21*a* and transport through the vacant spaces 23*e* in the direction away from the air inlet plate 21. It achieves the effect of transporting the air into the closed space 11 and producing the positive pressure airflow.

From the above descriptions, the present disclosure provides a positive airway pressure apparatus 100 having a micro pump 2 for producing a positive pressure airflow. The micro pump 2 is directly coupled with the mask 1. By utilizing the micro pump 2, the air outside the mask 1 is pumped into the mask 1 to form a positive pressure airflow. Comparing to the structure of ventilation hose 212 connected with breathing mask 214 and the vacuum pump of the body 210 in the prior art, the positive airway pressure apparatus 100 eliminates the use of the ventilation hose 212 and reduces the entire size. In that, the discomfort caused by wearing the conventional positive airway pressure apparatus 200 during sleep can be alleviated, and the portability of the positive airway pressure apparatus can be improved, and the patient can continue to wear for a long period of time without interrupting the treatment. The present disclosure is extremely valuable for industrial use.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A positive airway pressure apparatus for producing a positive pressure airflow, comprising:

a mask having a space;
a micro pump coupled to the mask and in fluid communication with the exterior of the mask, wherein the micro pump is a piezoelectric actuating pump and comprises:
   an air inlet plate;
   a resonance plate; and
   a piezoelectric actuator comprising:
      a suspension plate having a first surface, a second surface and a bulge, wherein the bulge is formed on the first surface;
      an outer frame arranged around the suspension plate and having a coupling surface;
      at least one bracket connected between the suspension plate and the outer frame for elastically supporting the suspension plate; and
      a piezoelectric element attached on the second surface of the suspension plate to drive the suspension plate to undergo the bending vibration in response to an applied voltage;
   wherein the at least one bracket is formed between the suspension plate and the outer frame as making the first surface of the suspension plate non-coplanar with the coupling surface of the outer frame and maintaining a chamber gap between the first surface of the suspension plate and the resonance plate;
   wherein the air inlet plate, the resonance plate, and the piezoelectric actuator are stacked and assembled sequentially; and
a processor electrically connected to the micro pump;
wherein when the processor transmits an actuation control signal to the micro pump, the micro pump is actuated in response to the actuation control signal and transports air from the exterior of the mask into the space to form the positive pressure airflow.

2. The positive airway pressure apparatus according to claim 1, wherein the piezoelectric actuating pump comprises:
the air inlet plate having at least one inlet, at least one convergence channel and a convergence chamber, wherein the at least one inlet allows the air to flow in, and the at least one convergence channel is corresponding in position to the at least one inlet and guides the air from the inlet toward the convergence chamber;
the resonance plate having a central aperture and a movable part, wherein the central aperture is facing the convergence chamber and the movable part surrounds the central aperture; and
the piezoelectric actuator corresponding in position to the resonance plate, wherein a chamber space is formed between the resonance plate and the piezoelectric actuator, so that the air from the at least one inlet of the air inlet plate is converged to the convergence chamber along the at least one convergence channel and flows into the chamber space through the central aperture of the resonance plate when the piezoelectric actuator is driven, whereby the air is further transported through a resonance between the piezoelectric actuator and the movable part of the resonance plate.

3. The positive airway pressure apparatus according to claim 1, wherein the piezoelectric actuating pump comprises a conducting plate and an insulation plate, and the air inlet plate, the resonance plate, the piezoelectric actuator, the insulation plate and the conducting plate are stacked and assembled sequentially.

4. The positive airway pressure apparatus according to claim 1, further comprising a pressure sensor disposed within the space of the mask to measure a pressure of the space to generate a detected pressure value and transmit the detected pressure value to the processor, wherein the detected pressure value is compared with a preset pressure value by the processor, so as to generate a pressure control signal according to the comparison result and transmit the pressure control signal to the micro pump, thereby regulating an air pressure output of the micro pump and ensuring the pressure of the space complying with the preset pressure value.

5. The positive airway pressure apparatus according to claim 1, further comprising a power module, wherein the power module is electrically connected to the processor for providing electrical energy.

6. The positive airway pressure apparatus according to claim 1, further comprising a pressure sensor disposed within the space of the mask to measure a pressure of the space to generate a plurality of detected pressure values and transmit the plurality of detected pressure values to the processor, wherein the detected pressure values are used to analyze a respiratory state by the processor, so as to generate a pressure control signal according to the respiratory state and transmit the pressure control signal to the micro pump, thereby increasing or decreasing an air pressure output of the micro pump.

7. The positive airway pressure apparatus according to claim 6, wherein when the processor determines that the respiratory state is an alternate point of inhalation and exhalation, the pressure control signal is generated and transmitted to the micro pump to decrease the air pressure output of the micro pump.

8. The positive airway pressure apparatus according to claim 6, wherein when the processor determines that the respiratory state is an abnormal state, the pressure control signal is generated and transmitted to the micro pump to increase the air pressure output of the micro pump.

9. A positive airway pressure apparatus for producing at least one positive pressure airflow, comprising:
   at least one mask having at least one space;
   at least one micro pump coupled to the at least one mask and in fluid communication with the exterior of the at least one mask, wherein the at least one micro pump is at least one piezoelectric actuating pump and comprises:
   at least one air inlet plate;
   at least one resonance plate; and
   at least one piezoelectric actuator comprising:
      at least one suspension plate having at least one first surface, at least one second surface and at least one bulge, wherein the at least one bulge is formed on the at least one first surface;
      at least one outer frame arranged around the at least one suspension plate and having at last one coupling surface;
      at least one bracket connected between the at least one suspension plate and the at least one outer frame for elastically supporting the at least one suspension plate; and
      at least one piezoelectric element attached on the at least one second surface of the at least one suspension plate to drive the at least one suspension plate to undergo the bending vibration in response to an applied voltage;
      wherein the at least one bracket is formed between the at least one suspension plate and the at least one outer frame as making the at least one first surface of the at least one suspension plate non-coplanar with the at least one coupling surface of the at least one outer frame and maintaining at least one chamber gap between the at least one first surface of the at least one suspension plate and the at least one resonance plate;
   wherein the at least one air inlet plate, the at least one resonance plate, and the at least one piezoelectric actuator are stacked and assembled sequentially; and
   at least one processor electrically connected to the at least one micro pump;
   wherein when the at least one processor transmits at least one actuation control signal to the at least one micro pump, the at least one micro pump is actuated in response to the at least one actuation control signal and transports air from the exterior of the at least one mask into the space to form the positive pressure airflow.

* * * * *